(12) United States Patent
VanDiepenbos et al.

(10) Patent No.: US 10,842,647 B2
(45) Date of Patent: Nov. 24, 2020

(54) FEMORAL INSERTER AND RETRACTOR (71) Applicant: Zimmer, Inc., Warsaw, IN (US)

(72) Inventors: Jeffery A. VanDiepenbos, Syracuse, IN (US); Nolan C. Jones, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 253 days.

(21) Appl. No.: 15/730,276

(22) Filed: Oct. 11, 2017

(65) Prior Publication Data
US 2018/0104070 A1 Apr. 19, 2018

Related U.S. Application Data
(60) Provisional application No. 62/408,257, filed on Oct. 14, 2016.

(51) Int. Cl.
*A61F 2/46* (2006.01)
*A61B 17/92* (2006.01)
*A61F 2/38* (2006.01)

(52) U.S. Cl.
CPC ............ *A61F 2/4603* (2013.01); *A61B 17/92* (2013.01); *A61F 2/461* (2013.01);
(Continued)

(58) Field of Classification Search
CPC .............. A61B 17/92; A61B 2017/922; A61B 2017/925; A61F 2/46; A61F 2/461;
(Continued)

(56) References Cited

U.S. PATENT DOCUMENTS 5,417,693 A 5/1995 Sowden et al.
5,732,992 A 3/1998 Mauldin
(Continued)

FOREIGN PATENT DOCUMENTS

DE 10013331 9/2001
WO 2018071543 4/2018

OTHER PUBLICATIONS

"International Application Serial No. PCT/US2017/056141, International Search Report dated Jan. 19, 2018", 6 pgs.
(Continued)

*Primary Examiner* — David W Bates
*Assistant Examiner* — Marcela I Shirsat
(74) *Attorney, Agent, or Firm* — Schwegman Lundberg & Woessner, P.A.

(57) ABSTRACT

Apparatuses and systems including at least one of mounting and removal of a femoral component on a femur are disclosed. The instrument can include a handle, a plunger, first and second arms and a knob. The handle can define a recess. The recess can extend along a portion of an elongate length of the handle. The plunger can be moveably disposed within the recess and can be configured to extend through an opening in a distal end of the handle to engage a pad to contact the pad against the femoral component. The first and second arms can be pivotally coupled to the handle and can be pivotable relative to one another. The first and second arms can each have at least one coupling feature configured to engage with a corresponding second coupling feature in the femoral component. The knob can be configured to operatively actuate the plunger to move the plunger proximal/distal within the recess to engage the plunger with and disengage the plunger from the pad. The instrument can reduce surgical time by providing a secure grasping and manipulation of the femoral component.

11 Claims, 6 Drawing Sheets

(52) U.S. Cl.
CPC ....... *A61B 2017/925* (2013.01); *A61F 2/3859* (2013.01); *A61F 2002/3895* (2013.01); *A61F 2002/4625* (2013.01)

(58) Field of Classification Search
CPC .................. A61F 2/4603; A61F 2/3859; A61F 2002/4627; A61F 2002/3895; A61F 2002/4625
USPC ............... 606/99, 91, 86 A, 86 B; 623/22.12
See application file for complete search history.

(56) References Cited

U.S. PATENT DOCUMENTS

| | | | |
|---|---|---|---|
| 9,220,611 B2 | 12/2015 | Jones et al. | |
| 9,782,877 B2* | 10/2017 | Marquis | B25B 27/02 |
| 9,925,066 B2* | 3/2018 | Khosla | A61F 2/461 |
| 2006/0149284 A1* | 7/2006 | McCormack | A61F 2/4611 606/99 |
| 2009/0312766 A1* | 12/2009 | McMillan | A61B 17/92 606/99 |
| 2010/0082074 A1* | 4/2010 | Long | A61F 2/4607 606/86 R |
| 2015/0051606 A1* | 2/2015 | Khosla | A61B 17/92 606/99 |

OTHER PUBLICATIONS

"International Application Serial No. PCT/US2017/056141, Written Opinion dated Jan. 19, 2018", 8 pgs.
"European Application Serial No. 17791521.2, Response to Communication pursuant to Rules 161(1) and 162 EPC filed Dec. 10, 2019", 18 pgs.
"European Application Serial No. 17791521.2, Communication Pursuant to Article 94(3) EPC dated Apr. 23, 2020", 3 pgs.

\* cited by examiner

FEMORAL INSERTER AND RETRACTOR

CLAIM OF PRIORITY

This application claims the benefit of U.S. Provisional Patent Application Ser. No. 62/408,257, filed on Oct. 14, 2016, the benefit of priority of which is claimed hereby, and which is incorporated by reference herein in its entirety.

FIELD

The present subject matter relates to orthopedic procedures and, more particularly, to instruments used in performing knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral component implanted on the distal end of the femur, which articulates with a tibial component implanted on the proximal end of a tibia to replicate the function of a healthy natural knee. Various types of arthroplasties are known including a total knee arthroplasty, where all of the articulating compartments of the joint are repaired with prosthetic components, and a unicompartmental knee arthroplasty, where only one damaged compartment of the knee is repaired with prosthetic components.

During a surgical procedure to implant a prosthetic knee joint, a provisional femoral component and a provisional tibial component can be placed on a distal femur and proximal tibia, respectively, after resecting the distal femur and proximal tibia. The provisional components assist with confirming the proper size and position of the permanent femoral and tibial components. The provisional components typically come in a range of sizes representative of the size and shape of the permanent components of the chosen prosthesis system. Provisional components are typically selected after making a preliminary determination of the proper size of the permanent components. A trial reduction of the knee joint with the provisional components in place may indicate that the preliminary size determination was not ideal. Alternative provisional components can then be selected and another trial reduction performed. After determining the proper size components, final prosthesis components are seated. Insertion and extraction of the provisional components and other components such as cut guides and the final prosthesis components can be performed with dedicated instruments.

OVERVIEW

The present inventors recognize, among other things, an instrument that facilitates easier more reliable grasping and manipulation of provisional and final prosthesis components. More particularly, the present inventors have recognized an instrument that can facilitate insertion and extraction of femoral components to facilitate placement and/or removal of the same during a surgical procedure. As such, the instrument can be configured to utilize grasping arms and a pad to contact the femoral component in conjunction with one another. The grasping arms can be biased to grip the femoral component to hold the femoral component to the instrument. A plunger can exert a compressive force on the pad (which in turn asserts a compressive force against the femoral component) to force the femoral component into place in a prepared femur.

To further illustrate the apparatuses and systems disclosed herein, the following non-limiting examples are provided:

Example 1 is an instrument for at least one of mounting and removal of a femoral component on a femur, the instrument can comprise: an handle defining a recess therein, the recess extending along a portion of an elongate length of the handle; a plunger moveably disposed within the recess and configured to extend through an opening in a distal end of the handle to engage a pad to hold the pad in contact with the femoral component; first and second arms pivotally coupled to the handle and pivotable relative to one another, the first and second arms each having at least one coupling feature configured to engage with a corresponding second coupling feature in the femoral component; and a knob configured to operatively actuate the plunger to move the plunger proximal/distal within the recess to apply a force on the pad.

In Example 2, the subject matter of Example 1 optionally can include the at least one coupling feature comprises a hooked tip and the second coupling feature comprises a notch configured to receive the hooked tip therein.

In Example 3, the subject matter of any one or more of Examples 1-2 optionally can include the first and second arms are each biased away from the handle by a spring, the spring exerts a force that attempts to close the first and second arm toward one another.

In Example 4, the subject matter of any one or more of Examples 1-3 optionally can include the plunger includes a slot configured to receive a pin that pivotally couples the handle to the first and second arms, and wherein the slot is configured to allow proximal and distal travel of the plunger relative to the handle, the first and second arms and the pin.

In Example 5, the subject matter of any one or more of Examples 1-4 optionally can include the plunger is coupled to the knob by a second spring, wherein the second spring is disposed within the recess and the second spring is configured to exert a force on the plunger when compressed by the knob.

In Example 6, the subject matter of any one or more of Examples 1-5 optionally can include the knob is disposed at a proximal end of the handle and is configured to thread into the handle to move proximal/distal relative thereto.

In Example 7, the subject matter of any one or more of Examples 1-6 optionally can include a second pin coupled to the handle, wherein the second pin is configured to limit at least one of a proximal and distal travel of the knob relative to the handle.

Example 8 is a system that can comprise: one or more femoral components each having a first notch disposed at a lateral side and a second notch spaced therefrom and disposed at a medial side of each of the one or more femoral components, each of the first and second notch defining an opening along the respective medial side and lateral side; and an instrument for at least one of mounting and removal of the femoral component on the femur, the instrument having first and second arms pivotally coupled to the handle and pivotable relative to one another, the first and second arms each having a hooked tip configured to insert in one of the first and second notch to engage the one or more femoral components.

In Example 9, the subject matter of Example 8 optionally can include the first and second arms are each biased by a spring away from the handle, the spring exerts a force that attempts to close the first and second arm toward one another such that the first and second arms exert compressive forces on the medial side and the lateral side of the one or more femoral components.

In Example 10, the subject matter of any one or more of Examples 8-9 optionally can include the instrument further includes: the handle defining a recess therein, the recess extending along a portion of an elongate length of the handle; a plunger moveably disposed within the recess and configured to extend through an opening in a distal end of the handle to engage a pad to hold the pad in contact with the femoral component; and a knob configured to operatively actuate the plunger to move the plunger proximal/distal within the recess to apply a force on the pad.

In Example 11, the subject matter of Example 10 optionally can include the plunger includes a slot configured to receive a pin that pivotally couples the handle to the first and second arms, and the slot is configured to allow proximal and distal travel of the plunger relative to the handle and the pin.

In Example 12, the subject matter of any one or more of Examples 10-11 optionally can include the plunger is coupled to the knob by a second spring, wherein the second spring is disposed within the recess and the second spring is configured to exert a force on the plunger when compressed by the knob.

In Example 13, the subject matter of any one or more of Examples 10-12 optionally can include the knob is disposed at a proximal end of the handle and is configured to thread into the handle to move proximal/distal relative thereto.

In Example 14, the subject matter of any one or more of Examples 8-13 optionally can include one or more pads configured to engage a surface of the one or more femoral components and be engaged by the instrument, wherein the one or more pads include both a medial notch along a medial side thereof and a lateral notch along a lateral side thereof, and wherein the medial notch and the lateral notch of the one or more pads are configured space a first surface of the medial side and a second surface of the lateral side of the one or more pads from the first and second arms respectively.

In Example 15, the subject matter of any one or more of Examples 8-14 optionally can include the one or more femoral components comprise a family of components each being differently sized from one another.

Example 16 is an instrument for at least one of mounting and removal of a femoral component on a femur, the instrument can comprise: an handle defining a recess therein, the recess extending along a portion of an elongate length of the handle; a plunger moveably disposed within the recess and configured to extend through an opening in a distal end of the handle to engage a pad to hold the pad in contact with the femoral component; first and second arms configured as jaws to pivotally couple to the handle and to pivot to close toward one another, the first and second arms each having a hooked tip configured to be received within a corresponding notch in a side of the femoral component; and a knob configured to operatively actuate the plunger to move the plunger proximal/distal within the recess to apply a force on the pad.

In Example 17, the subject matter of Example 16 optionally can include the plunger includes a slot configured to receive a pin that pivotally couples the handle to the first and second arms, and wherein the slot is configured to allow proximal and distal travel of the plunger relative to the handle and the pin.

In Example 18, the subject matter of any one or more of Examples 16-17 optionally can include the plunger is coupled to the knob by a second spring, wherein the second spring is disposed within the recess and the second spring is configured to exert a force on the plunger when compressed by the knob.

In Example 19, the subject matter of any one or more of Examples 16-18 optionally can include the knob is disposed at a proximal end of the handle and is configured to thread into the handle to move proximal/distal relative thereto.

In Example 20, the apparatuses or systems of any one or any combination of Examples 1-19 can optionally be configured such that all elements or options recited are available to use or select from.

These and other examples and features of the present apparatuses and systems will be set forth in part in the following Detailed Description. This Overview is intended to provide non-limiting examples of the present subject matter—it is not intended to provide an exclusive or exhaustive explanation. The Detailed Description below is included to provide further information about the present apparatuses and systems.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to devices and systems that can be used in various knee procedures including a total knee replacement procedure (TKA), a cruciate retaining total knee procedure, a unicompartmental knee replacement procedure, a bicompartmental knee replacement procedure comprised of two unicompartmental knee replacements, a procedure that utilizes a single (total) femoral component and two unicompartmental tibial components, and other types of knee replacement procedures. Because the instruments of the present disclosure is usable with both provisional and final prosthesis components, "femoral components" will be generically used in this document to denote either a provisional or a final prosthesis component.

The disclosed devices include an instrument (sometimes referred to as an inserter or impactor tool herein) for mounting on and/or removing a femoral component from a femur. The instrument can include a handle, a plunger, first and second arms and a knob. The handle can define a recess. The recess can extend along a portion of an elongate length of the handle. The plunger can be moveably disposed within the recess and can be configured to extend through an opening in a distal end of the handle to engage a pad to contact the pad against the femoral component. The first and second arms can be pivotally coupled to the handle and can be pivotable relative to one another. The first and second arms can each have at least one coupling feature configured to engage with a corresponding second coupling feature in the femoral component. The knob can be configured to operatively actuate the plunger to move the plunger proximal/distal within the recess to engage the plunger with and disengage the plunger from the pad. The instrument can reduce surgical time by providing a secure grasping and manipulation of the femoral component.

The instruments described herein can utilize a pad to contact the femoral component. The pads can be constructed of polyphenylsulfone and other biologically stable polymer such as ultra-high weight polyethylene. Further details regarding construction of the pad can be found in U.S. Pat. No. 9,220,611, the entire disclosure of which is incorporated herein by reference.

Figure 1:
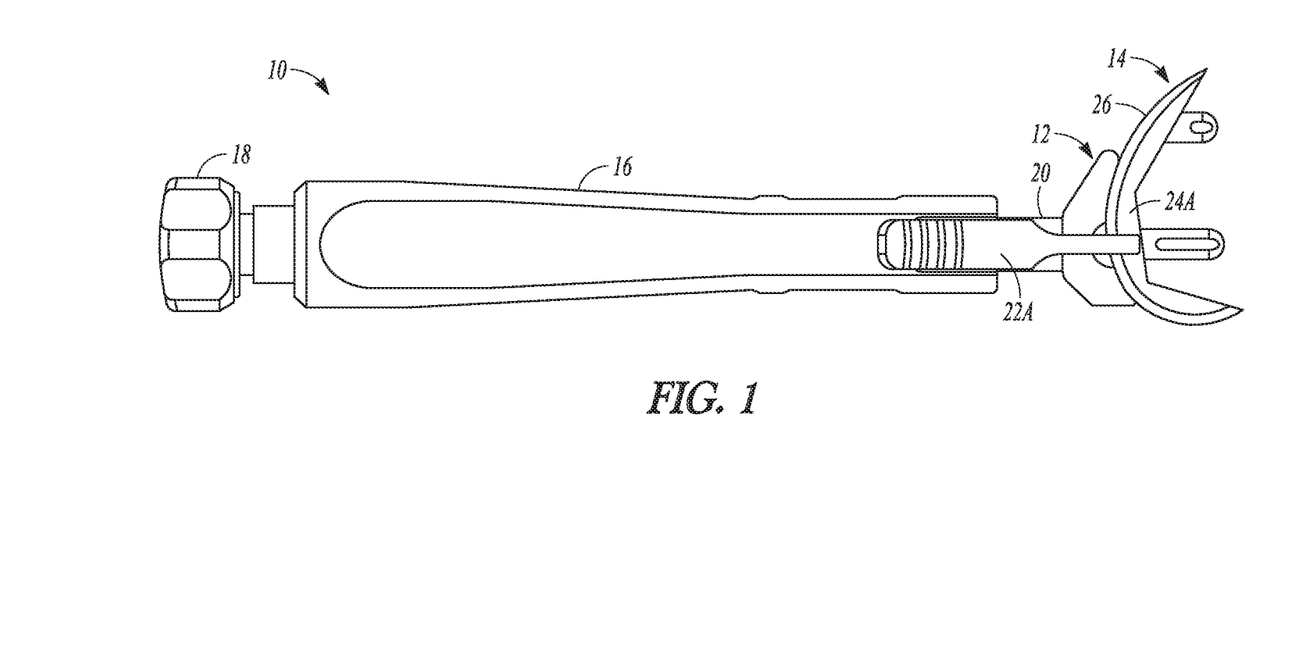
FIG. 1 is a perspective view of instrument engaging a pad and a femoral component according to an example of the present application.

FIG. 1 illustrates an instrument 10 configured to engage a pad 12 and a femoral component 14. The instrument 10 can include a handle 16, a knob 18, a plunger 20 and first and second arms (only the first arm 22A is shown in FIG. 1).

The handle 16 can be configured to receive the plunger 20 and portions of the knob 18 therein. The knob 18 can couple with the plunger 20 as will be described in further detail subsequently. The first arm 22A (and second arm not shown) can couple to the handle 16 via a pin. The first arm 22A (and the second arm) can be configured to engage with the femoral component 14 along medial and lateral sides (only medial side 24A is shown in FIG. 1) thereof. The plunger 20 can be moveable relative to the handle 16 and the first arm 22A to engage and disengage with the pad 16. The pad 16 can engage with a distal surface 26 of the femoral component 14.

During use the first and second arms (only the first arm 22A is shown) can be biased to grasp the femoral component 14 along the medial and lateral sides (only medial side 24A is shown in FIG. 1) to hold the femoral component 14 to the inserter. The plunger 20 via turning of the knob 18 can exert a compressive force on the pad 12 (which in turn asserts a compressive force against the femoral component 14) to force the femoral component 14 into place in the prepared femur (now shown). During this process the pad 12 can be captured between the plunger 20 and the femoral component 14.

As shown in the example of FIG. 1, the femoral component 14 can be use in a unicompartmental knee replacement procedure (sometimes referred to as a "unicondylar" knee replacement procedure or "UKA") where one of the medial and lateral condyles of the femur is resected. Further resection is performed to remove one of the medial articular surface and the lateral articular surface of the tibia can be performed in a UKA. Femoral cutting apparatuses can be utilized to remove corresponding articular surfaces of the femur that would otherwise interface with either the medial articular surface or the lateral articular surface of the tibia. Prostheses such as the femoral component can be implanted on the femur and the tibia providing for the replaced articular surfaces. Other portions of the knee, e.g., the intercondylar eminence, tissues (e.g., ACL, PCL, etc.) can be maintained in the UKA. In a bicompartmental knee replacement procedure, both the medial and lateral condyles of the femur are resected and the medial articular surface and the lateral articular surface of the tibia are also resected. Similar to a unicompartmental knee replacement procedure, the bicompartmental knee replacement procedure maintains portions of the knee such as the intercondylar eminence. Similarly, a knee replacement procedure that could utilize a total femoral component and two unicompartmental tibial components can seek to maintain portions of the knee such as the intercondylar eminence. The femoral component 14 designed for one of these knee procedures (e.g., the unicompartmental knee procedure, bicompartmental knee procedure, etc.) are shown in FIG. 1 for exemplary purposes. It is recognized that the instruments described herein can be used with other types of knee procedures including a total knee procedure.

Figure 2:
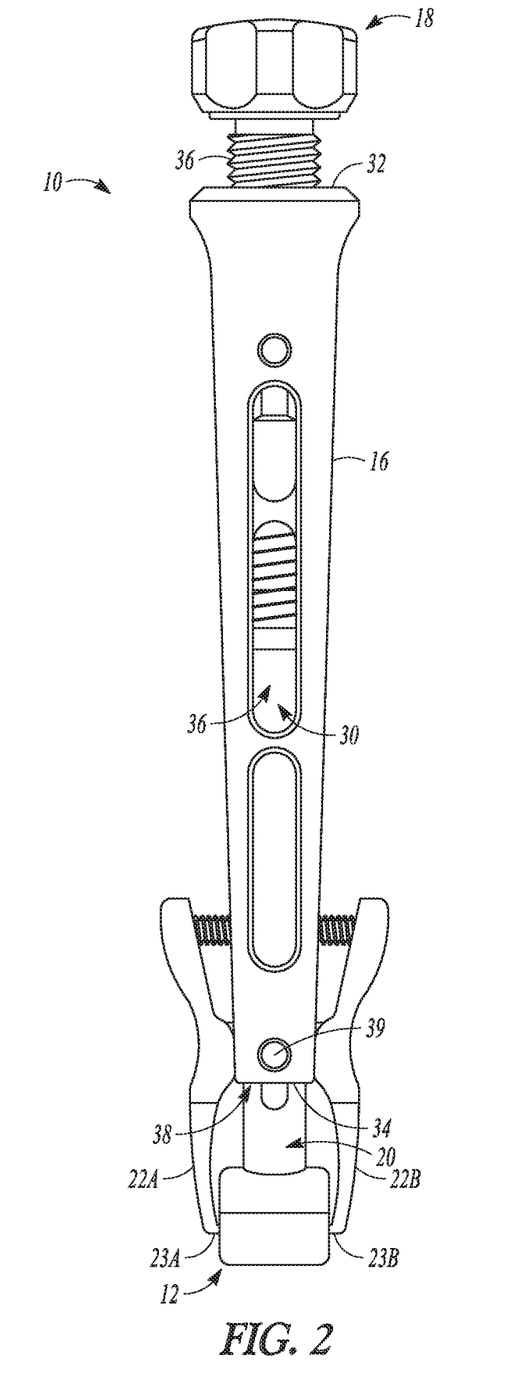
FIG. 2 is a perspective view of the instrument and the pad of FIG. 1 according to an example of the present application.
Figure 2A:
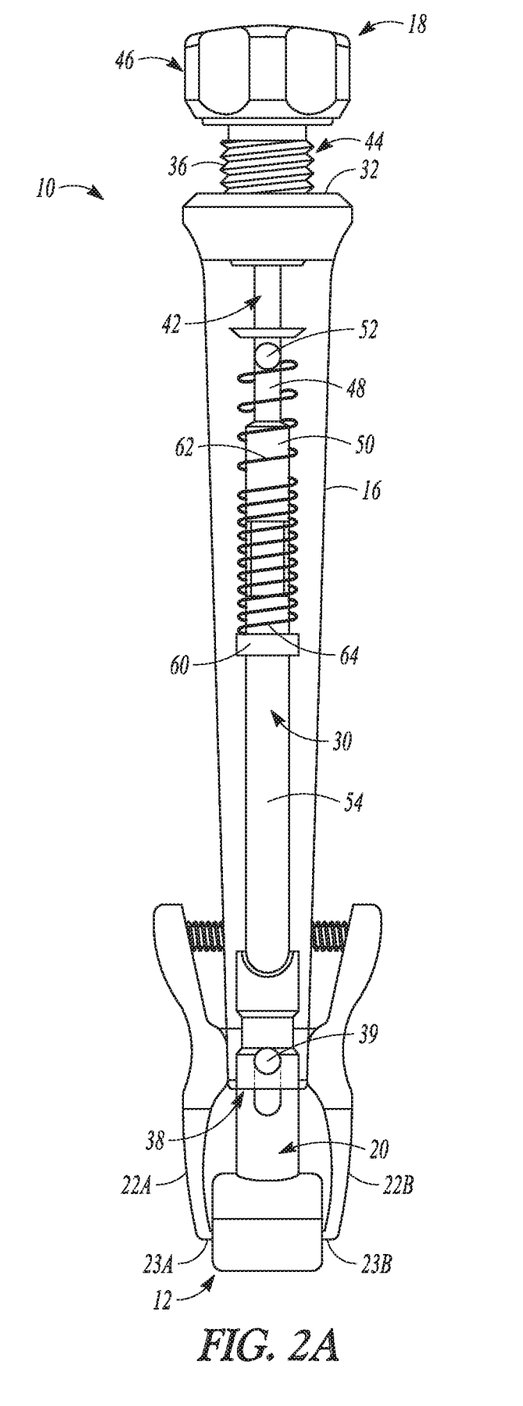
FIG. 2A is a perspective view of the instrument of FIG. 2, with portions of a handle removed to show a portions of a plunger and knob according to an example of the present application.

FIGS. 2 and 2A show the instrument 10 and the pad 12. As discussed previously in reference to FIG. 1, the instrument 10 can include the handle 16, the knob 18, the plunger 20 and the first and second arms 22A and 22B. FIG. 2A shows portions of the handle 16 removed to show portions of the knob 18 and the plunger 20 that can be configured to be disposed within a recess 30 that extends along an elongate length of the handle 16 from a proximal end 32 of the handle 16 to a distal end 34 thereof.

As shown in FIG. 2, the handle 16 can have openings 36 to view into the recess 30 to visualize the knob 18 and the plunger 20 as well as other components. The knob 18 can be configured to couple with the handle 16. More particularly, the knob 18 can be disposed at the proximal end 32 of the handle 16 and can extend into the recess 30. The knob 18 can be configured to thread (using threads 36) into the handle 16 (into the recess 30) to move proximal/distal relative to the handle 16. As will be discussed in further detail subsequently, the knob 18 can be configured to operatively actuate the plunger 20 to move the plunger 20 proximal/distal within the recess 30 to apply a force on the pad 12.

FIGS. 2 and 2A show the plunger 20 can be moveably disposed within the recess 30 of the handle 16. The plunger 20 can be configured to extend through an opening 38 at the distal end 34 of the handle 16 to engage the pad 12. Such engagement can hold the pad in contact with the femoral component 14 as shown previously in FIG. 1.

The first and second arms 22A and 22B can be disposed adjacent the distal end 34 of the handle 16 and can extend further distal of the distal end 34. The first and second arms 22A and 22B can be pivotally coupled to the handle 16 via a first pin 39. The first and second arms 22A and 22B can be configured as levers to be pivotable relative to one another as well as the handle 16. As will be described in further detail subsequently, the first and second arms 22A and 22B can each have at least one coupling feature 23A and 23B configured to engage with a corresponding second coupling feature 23AA and 23BB (shown in FIG. 5) in the femoral component 14 (refer to FIGS. 5 and 5A).

Figure 3:
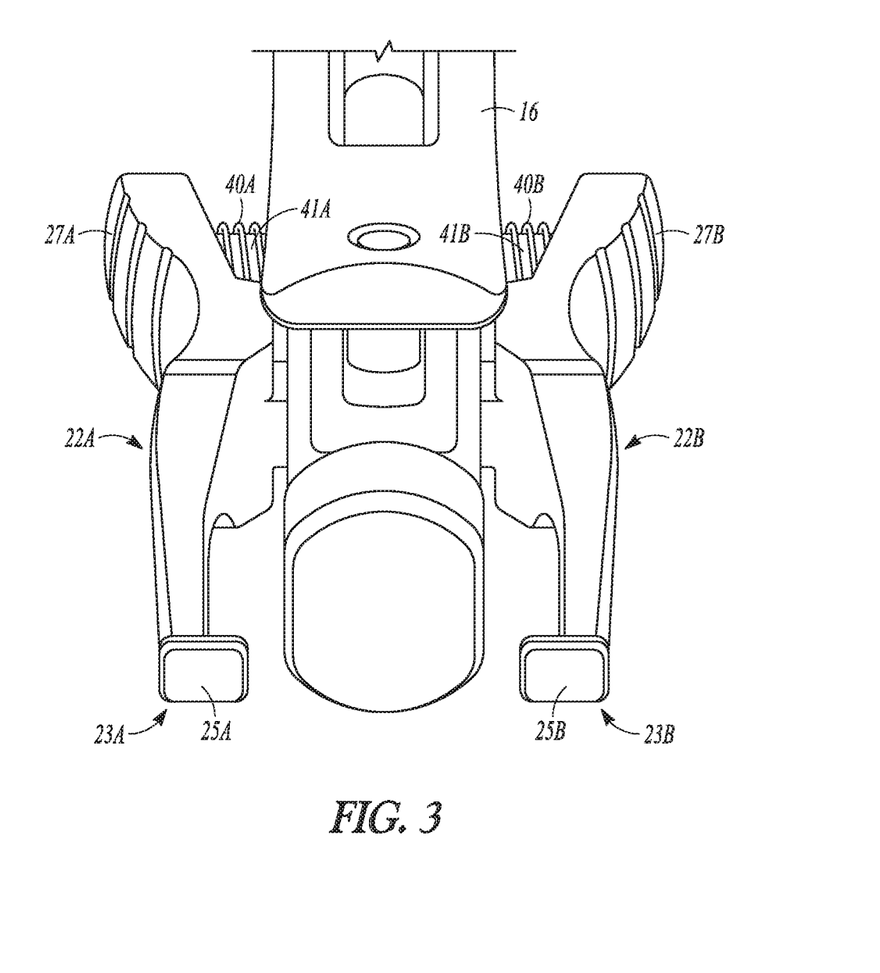
FIG. 3 is an enlarged perspective view of a portion of the instrument of FIGS. 2 and 2A showing arms according to an example of the present application.

According to the example of FIG. 3, the at least one coupling feature 23A and 23B can comprise a hooked tip 25A and 25B where the first and second arms 22A and 22B can change direction at a distal end portion thereof. The change of direction (i.e. the hook) extends the distal ends of the first and second arms 22A and 22B toward one another.

As shown in FIG. 3, the first and second arms 22A and 22B can each be biased away from the handle 16 by a spring 40A and 40B. The spring 40A and 40B can extend between the handle 16 and the first and second arms 22A and 22B, respectively. According to the example of FIGS. 2 and 2A, the spring 40A and 40B can be received on a corresponding projection 41A and 41B of the handle 16. In operation, the spring 40A and 40B can be configured to exert a force on a proximal portion 27A and 27B of the respective first and second arm 22A and 22B. This force can attempt to close the first and second arms 22A and 22B toward one another such that the first and second arms 22A and 22B can act as jaws. The force can engage of the first and second arms 22A and 22B with the femoral component 14 (as shown in FIG. 1) when the instrument 10 is manipulated and properly placed. The force can be overcome by the user pressing on the proximal portion 27A and 27B of the first and second arms 22A and 22B to overcome the force and actuate the first and second arms 22A and 22B away from one another (and out of engagement with the femoral component 14 (FIG. 1).

Returning to FIG. 2A, the plunger 20 and the knob 18 can include portions internal to the recess 30. Thus, the knob 18 can include a rod portion 42, a threaded portion 44 (that can include threads 36) and an actuator portion 46. The rod portion 42 can include a necked down section 48 and a distal section 50.

As shown in FIG. 2A, the actuator portion 46 can be configured to extend proximal of the proximal end 32 of the handle 16 and can connect with the threaded portion 44. The treaded portion 44 can connect with the rod portion 42. The rod portion 42 can be configured to be received within and extend along a longitudinal length of the recess 30. The necked down section 48 can be connected to the distal section 50. The distal section 50 of the rod portion 42 can have a relatively larger circumference in cross section relative to the necked down section 48. A second pin 52 can be disposed within and coupled to the handle 16 (as shown in FIG. 2) and can extend inward into the recess 30 to interface with the rod portion 42. The second pin 52 can be disposed so as not to make contact with the necked down section 48, thereby allowing for movement of knob 18. However, the second pin 52 can be disposed so as to make contact with the distal section 50. This can keep the knob 18 from being entirely removable from the handle 16 without removal of the second pin 52. Thus, the second pin 52 can be configured to limit at least one of a proximal and distal travel of the knob 18 relative to the handle 16.

As shown in the example of FIG. 2A, the plunger 20 can include a rod portion 54 and a body portion 56. The body portion 56 can include a slot 58 therein. The rod portion 54 can include a flange 60.

The body portion 56 of the plunger 20 can connect with the rod portion 54 and can be disposed distal thereto. The rod portion 54 can be received in and can extend along a longitudinal length of the recess 30. The body portion 56 can extend from the opening 38 of the recess 30 and can be disposed between the first and second arms 22A and 22B. The slot 58 can be disposed in the body portion 56 and can extend longitudinally therealong. The slot 58 can be configured to receive the first pin 39 therein. The slot 58 can be configured to allow proximal and distal travel of the plunger 20 relative to the handle 16, the first and second arms 22A and 22B and the first pin 39.

As shown in FIG. 2A, the first flange 60 can extend from the rod portion 54. The first flange 60 can be configured to provide a base/stop for one or more springs. The one or more springs can comprise a first spring 62 and a second spring 64 according to the example of FIG. 2A. The first spring 62 can extend further longitudinally proximal of the second spring 64. The first spring 62 can be configured to contact the second pin 52 at a proximal end thereof. The first spring 62 can supply a first force to the plunger 20 via the first flange 60. The first force can be sufficient to provide for initial engagement between the plunger 20 and the pad 12. However, in some cases the first force may not be sufficiently strong such that the user cannot move the plunger 20 and pad 12 in the proximal direction load the pad 12 between the first and second arm 22A and 22B, for example.

The second spring 64 can be disposed within the recess 30 between the distal section 50 and the rod portion 54 and can contact the first flange 60 at a distal end thereof. The plunger 20 can be coupled to the knob 18 by the second spring 64. More particularly, the second spring 64 can be configured to exert a second force on the plunger 20 when compressed by the knob 18. This second force can be applied when the knob 18 is threaded distally into the handle 16. The second force can be exerted through the plunger 20 to the pad 12 and can provide a further engaging force for rigidly holding the pad 12 to the femoral component.

Figure 4:
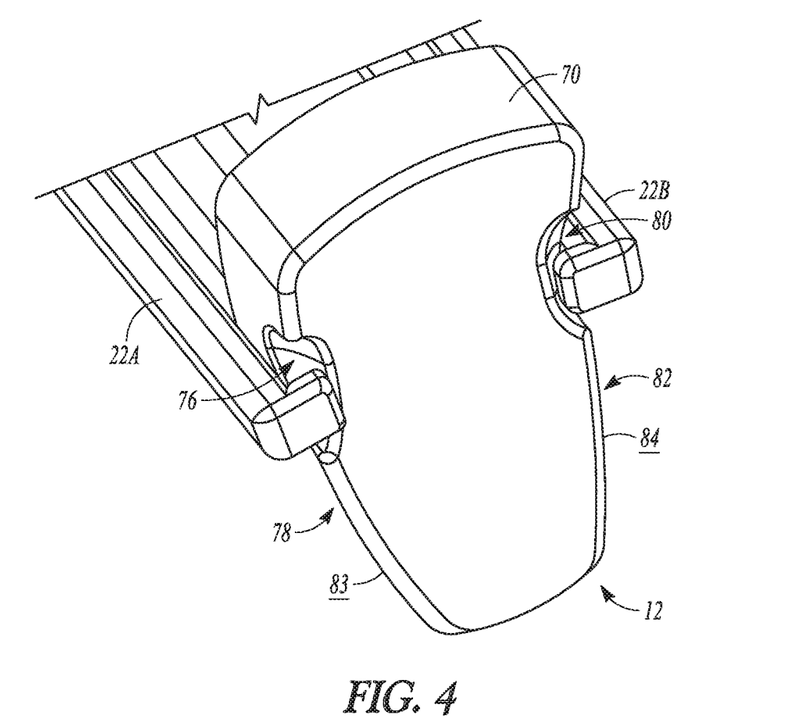
FIG. 4 is an enlarged perspective view of the arms and pad according to an example of the present application.
Figure 4A:
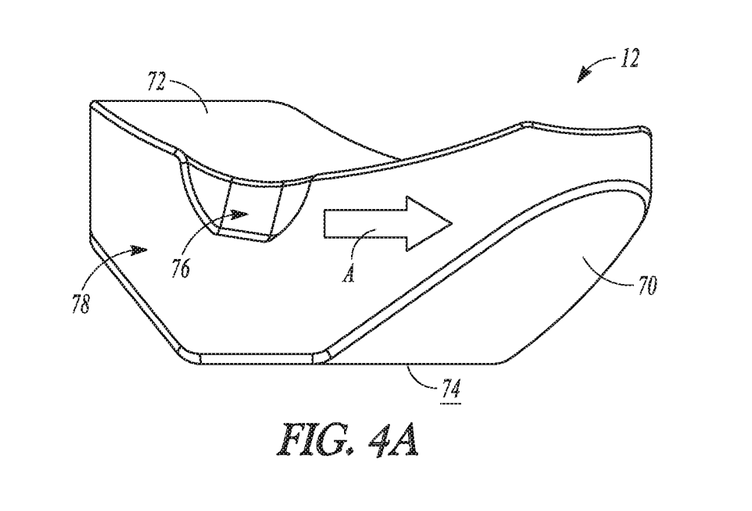
FIG. 4A is a perspective view of the pad according to an example of the present application.

As shown in FIGS. 4 and 4A, the pad 12 can be marked with indicia 70 indicating a posterior and anterior of the pad 12 for engagement against the femoral component. The pad 12 can have further indicia such as arrows A (FIG. 4A) pointing toward the anterior for reference by the physician. As is further illustrated in FIGS. 4 and 4A, according to some examples the pad 12 can configured to engage a surface of the one or more femoral components along surface 72 and can be engaged by the instrument on an opposing surface 74 (shown in FIG. 4A only). The pad 12 can include both a medial notch 76 along a medial side 78 thereof and a lateral notch 80 along a lateral side 82 (both shown in FIG. 4 only) thereof. The medial notch 76 and the lateral notch 80 can be configured space a surface 83 of the medial side 78 and a surface 84 of the lateral side 82 of the pad 12 from the first and second arms 22A and 22B as shown in FIG. 4. Thus, the medial notch 76 and the lateral notch 80 can provide relief for the pad 12 from engaging the first and second arms 22A and 22B.

Figure 5:
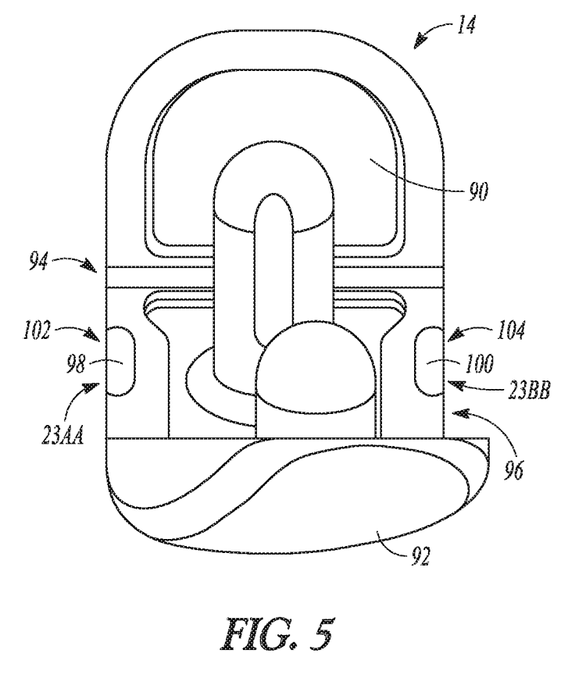
FIGS. 5 and 5A are a perspective views of the femoral component having recesses along medial and lateral sides thereof according to an example of the present application.
Figure 5A:
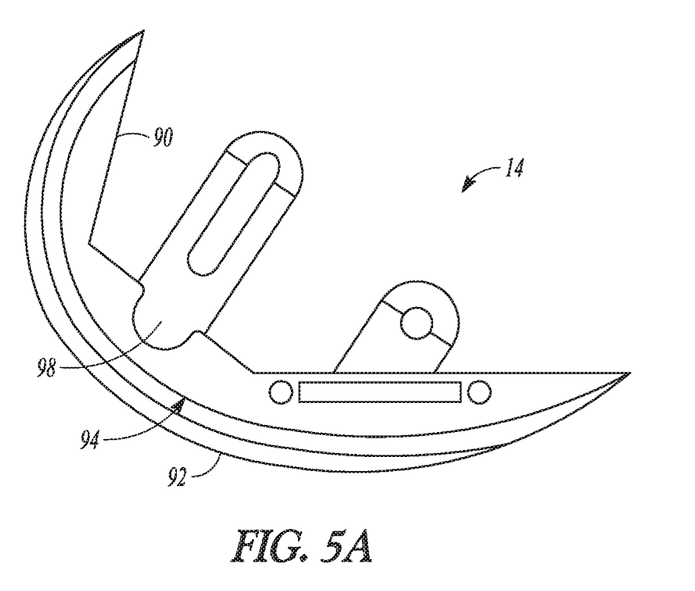

FIGS. 5 and 5A show the femoral component 14 from various perspectives. As shown in FIG. 5, the femoral component 14 can include a bone interfacing surface 90, an articular surface 92, a medial side 94, a lateral side 96, a first notch 98 and a second notch 100.

The bone interfacing surface 90 can be disposed on an opposing side of the femoral component 14 from the articular surface 92. The bone interfacing surface 90 can be configured to seat on and have pegs or other coupling features that can seat in the resected surface of the femur. The medial side 94 and the lateral side 96 can separate the bone interfacing surface 90 from the articular surface 92. The medial side 94 can be spaced from and opposing the lateral side 96. The first notch 98 (shown in both FIGS. 5 and 5A) can be disposed at the medial side 94 (shown in both FIGS. 5 and 5A) and the second notch 100 can be spaced therefrom and disposed at the lateral side 96. The first and second notches 98, 100 can be recessed from the articular surface 92 and the bone interfacing surface 90. Each of the first and second notch 98, 100 can define an opening 102, 104 along the respective medial side 94 and lateral side 96. Each of the first and second notch 98, 100 can be configured to receive one of the respective hooked tips 25A, 25B (FIG. 3) therein via the respective opening 102, 104.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. An instrument for at least one of mounting and removal of a femoral component on a femur, the instrument comprising:
   a pad configured to engage the femoral component;
   a handle configured to be graspable by a user of the instrument, the handle defining a recess therein, the recess extending along a portion of an elongate length of the handle;
   a plunger moveably disposed within the recess and attached to the pad, wherein the plunger is configured to extend through an opening in a distal end of the handle and extend distal of the handle to attach to the pad, and wherein the plunger is configured to hold the pad in contact with the femoral component;
   first and second arms pivotally coupled to the handle and pivotable relative to one another, the first and second arms each having at least one coupling feature configured to engage with a corresponding second coupling feature in the femoral component;
   a knob configured to operatively actuate the plunger to move the plunger proximal/distal within the recess to apply a force on the pad;
   a first spring configured to bias each of the first and second arms away from the handle, the first spring is configured to exert a force that attempts to close the first and second arm toward one another;
   a second spring coupling the plunger to the knob, wherein the second spring is disposed within the recess and the second spring is configured to exert a force on the plunger when compressed by the knob; and
   a pin that pivotally couples the handle to the first and second arms, wherein the pin is received in a slot of the plunger, and wherein the slot is configured to allow proximal and distal travel of the plunger relative to the handle, the first and second arms and the pin.

2. The apparatus of claim 1, wherein the at least one coupling feature comprises a hooked tip and the second coupling feature comprises a notch configured to receive the hooked tip therein.

3. The apparatus of claim 1, wherein the knob is disposed at a proximal end of the handle and is configured to thread into the handle to move proximal/distal relative thereto.

4. The apparatus of claim 1, further comprising a second pin coupled to the handle, wherein the second pin is configured to limit at least one of a proximal and distal travel of the knob relative to the handle.

5. An instrument for at least one of mounting and removal of a femoral component on a femur, the instrument comprising:
   a pad configured to engage the femoral component;
   a handle configured to be graspable by a user of the instrument, the handle defining a recess therein, the recess extending along a portion of an elongate length of the handle;
   a plunger moveably disposed within the recess and attached to the pad, wherein the plunger is configured to extend through an opening in a distal end of the handle and extend distal of the handle to attach to the pad, and wherein the plunger is configured to hold the pad in contact with the femoral component;
   first and second arms configured as jaws pivotally coupled to the handle, wherein the jaws pivot toward one another to close, the first and second arms each having a hooked tip configured to be received within a corresponding notch in a side of the femoral component;
   a knob configured to operatively actuate the plunger to move the plunger proximal/distal within the recess to apply a force on the pad, wherein the knob is disposed at a proximal end of the handle and is configured to thread into the handle to move proximal/distal relative thereto;
   a spring coupling the plunger to the knob, wherein the spring is disposed within the recess and the spring is configured to exert a force on the plunger when compressed by the knob; and a pin that pivotally couples the handle to the first and second arms, wherein the pin is received in a slot of the plunger, wherein the slot is configured to allow proximal and distal travel of the plunger relative to the handle, the first and second arms and the pin, and wherein the threading of the knob allows for adjustment of the plunger relative to the handle, the first and second arms and the pin.

6. An instrument for at least one of mounting and removal of a femoral component on a femur, the instrument comprising:

a pad configured to engage the femoral component;

a handle configured to be graspable by a user of the instrument, the handle defining a recess therein, the recess extending along a portion of an elongate length of the handle;

a plunger moveably disposed within the recess and attached to the pad, wherein the plunger is configured to extend through an opening in a distal end of the handle and extend distal of the handle to attach to the pad, and wherein the plunger is configured to hold the pad in contact with the femoral component;

first and second arms pivotally coupled to the handle and pivotable relative to one another, the first and second arms each having at least one coupling feature configured to engage with a corresponding second coupling feature in the femoral component;

a knob configured to operatively actuate the plunger to move the plunger proximal/distal within the recess to apply a force on the pad;

a first pin that pivotally couples the handle to the first and second arms; and a second pin coupled to the handle, wherein the second pin is configured to limit at least one of a proximal and distal travel of the knob relative to the handle.

7. The apparatus of claim 6, wherein the plunger includes a slot configured to receive the first pin, wherein the slot is configured to allow proximal and distal travel of the plunger relative to the handle, the first and second arms and the first pin.

8. The apparatus of claim 6, wherein the knob is disposed at a proximal end of the handle and is configured to thread into the handle to move proximal/distal relative thereto.

9. The apparatus of claim 6, wherein the at least one coupling feature comprises a hooked tip and the second coupling feature comprises a notch configured to receive the hooked tip therein.

10. The apparatus of claim 6, wherein the first and second arms are each biased away from the handle by a spring, the spring exerts a force that attempts to close the first and second arm toward one another.

11. The apparatus of claim 10, wherein the plunger is coupled to the knob by a second spring, wherein the second spring is disposed within the recess and the second spring is configured to exert a force on the plunger when compressed by the knob.

* * * * *